United States Patent [19]

Fujiura et al.

[11] Patent Number: 5,002,986

[45] Date of Patent: Mar. 26, 1991

[54] FLUID ABSORBENT COMPOSITIONS AND PROCESS FOR THEIR PREPARATION

[75] Inventors: Yoji Fujiura; Takashi Sumiya, both of Kyoto, Japan

[73] Assignee: Hoechst Celanese Corporation, Somerville, N.J.

[21] Appl. No.: 317,230

[22] Filed: Feb. 28, 1989

[51] Int. Cl.$^5$ .................... C08G 63/48; C08G 63/91; C08F 8/14; C08F 20/02

[52] U.S. Cl. ........................ 524/47; 524/734; 525/54.23; 525/54.26; 525/54.32; 525/330.1; 525/330.2; 525/370; 525/371; 525/372; 527/300

[58] Field of Search ............... 524/47, 734; 525/54.23, 525/54.26, 54.32, 330.1, 330.2, 370, 371, 372; 527/300

[56] References Cited

U.S. PATENT DOCUMENTS

| | | | |
|---|---|---|---|
| 4,043,952 | 8/1977 | Ganslaw et al. | 527/201 |
| 4,286,082 | 8/1981 | Tsubakimoto et al. | 526/240 |
| 4,295,987 | 10/1981 | Parks | 252/194 |
| 4,302,369 | 11/1981 | Elmquist | 524/734 |
| 4,500,670 | 2/1985 | McKinley et al. | 524/454 |
| 4,587,308 | 5/1986 | Makita et al. | 525/373 |
| 4,654,039 | 3/1987 | Brandt et al. | 526/207 |
| 4,734,478 | 3/1988 | Tsubakimoto et al. | 527/300 |
| 4,771,105 | 9/1988 | Shirai et al. | 525/54.23 |

*Primary Examiner*—Nathan M. Nutter
*Attorney, Agent, or Firm*—Hugh C. Crall

[57] ABSTRACT

This invention relates to fluid absorbent polymer compositions having the ability to absorb aqueous ionic fluids and water rapidly and efficiently. These fluid absorbent polymer compositions are prepared from fine base polymer particles which are ionically surface crosslinked and agglomerated into larger particles by the use of high energy mixing conditions. The fluid absorbent compositions of the invention find application in the preparation of absorbent articles such as diapers, sanitary napkins and incontinent devices.

21 Claims, No Drawings

FLUID ABSORBENT COMPOSITIONS AND PROCESS FOR THEIR PREPARATION

BACKGROUND OF THE INVENTION

1. Field of the Invention

This invention relates to fluid absorbent polymer compositions having the capability to absorb large volumes of aqueous fluids rapidly and efficiently.

2. Related Art

Various attempts have been made to produce fluid absorbent polymer compositions that have a high rate of fluid uptake or absorbency. Compositions possessing a high absorbency rate are desired for use in diapers, sanitary napkins and particularly in adult incontinent devices where a large amount of urine must be absorbed rapidly in order to avoid leakage and/or an unpleasant wetness.

One such attempt is reported in U.S. Pat. No. 4,734,478 where fluid absorbent polymer particles are covalently surface crosslinked with a solution containing 0.001 to 10 parts by weight of a polyhydric alcohol, 0.01 to 80 parts by weight of a hydrophillic organic solvent and 0 to 8 parts by weight of water per 100 parts of absorbent polymer and heating the mixture at a temperature of at least 90° C. to react the fluid absorbent polymer with the polyhydric alcohol. This patent also discloses the use of high-speed or high intensity mixers to effect mixing of the polymer particles with the polyhydric alcohol which results in the agglomeration of the wetted polymer particles. The addition of finely divided silica to the covalently surface crosslinked absorbent polymer is also disclosed. The addition of finely divided silica and other inorganic materials to water absorbent polymers is also disclosed in various other U.S. Patents; see for example, U.S. Pat. Nos. 4,286,082 (added after crosslinking), 4,587,308 (added during crosslinking), and 4,500,670 (synthetic silicate and other inorganic powders to increase gel strength).

The surface crosslinking of fluid absorbent polymers is disclosed in U.S. Pat. Nos. 4,043,952 and 4,295,987. The '952 patent discloses conducting the surface crosslinking using a organic liquid or a mixture of an organic liquid and water as the dispersing medium. The '987 patent teaches the use of a divalent ionic crosslinker.

It is the object of this invention to provide a fluid absorbent polymer composition that absorbs water and aqueous ionic fluids at a high absorbency rate. This object is accomplished by the surface crosslinking with an ionic crosslinker and agglomeration of a base absorbent polymer having a fine particle size distribution into larger particles. In the following description of the invention surface crosslinking and crosslinker (in the context of the invention) means ionic surface crosslinking or an ionic crosslinker.

SUMMARY OF THE INVENTION

This invention relates to fluid absorbent polymer compositions having the capability to rapidly absorb aqueous fluids, a process for their preparation and absorbent articles prepared therefrom such as diapers.

The water absorbent compositions of the invention have an absorbency rate of 20 seconds or less and comprise water absorbent polymer particles having a free absorbency of at least 30 ml/gm which have been surface crosslinked and agglomerated under high intensity mixing conditions into larger particles. The base polymer particles in addition to having a free absorbency of at least 30 ml/gm should have a particle size distribution such that 100 percent of the particles are smaller than 300 microns and wherein at least 40 percent of said particles are 150 microns or smaller.

The absorbent compositions of the invention are prepared by introducing the above described absorbent base polymer particles into a high intensity mixing zone and contacting them with an aqueous solution of an ionic crosslinking agent in an amount of about 1 to 20 percent by weight containing about 0.05 to 10 percent by weight of an ionic crosslinking agent. The ionic crosslinking agents useful in the invention are from water soluble organic or inorganic compounds capable of providing in aqueous solution an ionized metal cation, an amino or an imino cation having a valence of at least two.

DESCRIPTION OF THE PREFERRED EMBODIMENTS

The invention is that of a fluid absorbent polymer composition having a high rate of absorbency and a process for its preparation. The absorbent polymer compositions of the invention are surface crosslinked and agglomerated absorbent polymer particles having an absorbency rate of 20 seconds or less. The high absorbency rate polymer compositions of the invention find application in the preparation of diapers, sanitary napkins and particularly in the preparation of adult incontinent devices.

The fluid absorbent polymer compositions of the invention comprise fluid absorbent base polymers having a fine particle size distribution which have been surface crosslinked and agglomerated into larger particles under high intensity mixing conditions. These absorbent polymer compositions have the ability to absorb aqueous fluids rapidly and efficiently.

Absorbency rate as used in this description is determined by the following procedure. A 1.59 percent (weight/volume) saline(NaCl) solution containing a water soluble dye is prepared. Any dye may be used in an amount sufficient to impart color to the solution (e.g. 0.001 grams of Brilliant Cresyl Blue per 1000 ml). The dyed saline solution is thoroughly stirred to ensure dissolution and brought to a temperature of 25° C. ±0.5° C. One gram of absorbent polymer is then distributed evenly over the bottom surface of a 57 mm-diameter, aluminum dish (Fisher #08-732). The saline solution in an amount of 30 ml is rapidly poured into the middle of the dish in less than ½ second. Rapid addition of the saline solution should create a turbulent action and suspension of the polymer. Timing with a stopwatch is started as soon as the saline solution touches the polymer and the sample is observed at a distance of 12–15 inches above the dish. Timing is stopped when the contents of the dish have gelled. "Gelled", is defined as the point where free solution is not observed on the surface of the sample. Five such tests are run on each sample and the average time is determined. The fluid absorbent polymer compositions of the invention are prepared from fine absorbent base polymers having a free absorbency of at least 30 ml per gram as determined by the above described test.

The absorbent base polymers prior to ionic surface crosslinking and agglomeration, should have a fine particle size distribution wherein 100 percent of the particles are smaller than 300 microns and at least 40 percent are smaller than 150 microns; preferably 100 percent of the particles are 150 microns or smaller; most preferably 100 microns of less. Particle size distribution is generally reported in mesh size and as used in this description is correlated to microns using the following conversion factors: 50 mesh–300 microns, 100 mesh–150 microns, 140 mesh–100 microns and 200 mesh–75 microns. Mesh size, as reported herein, is the U.S. Sieve Series.

Studies conducted on different particle size distributions generally show that the finer the particle size prior to surface crosslinking and agglomeration, the faster the absorbency rate of the crosslinked and agglomerated particles. Although the agglomerated particles when examined under a scanning electron microscope do not show any intra-particle boundaries, it is believed, without being bound to any particular theory, that the ionically surface crosslinked and agglomerated particles when wetted exhibit a higher apparent surface area than would be expected for a solid particle of that size and hence an unexpectedly high absorbency rate is attained.

The uniformity of the ionic surface crosslinking of the base polymer has a significant effect on the absorbency rate of the absorbent compositions of the invention; i.e., the more uniform the surface crosslinking, the faster the absorbency rate. Uniform ionic surface crosslinking is, of course, achieved by uniform distribution of the crosslinker solution on the surfaces of the base polymer particles prior to agglomeration. Factors influencing uniform distribution of the crosslinker solution on the surface of the base polymer particles are: the concentration of crosslinker solution, the degree of dispersion of the crosslinker solution prior to contact with the base polymer particle's surfaces, the particles size of the base polymer, the uniformity of mixing in the mixing zone, the rate of reaction of the crosslinker and other such factors which promote uniform coating of the base polymer particles with the crosslinker solution.

In addition to the particle size distribution of the base polymer and uniformity of crosslinking, it has been found that the surface characteristic (which influences crosslinking uniformity) of the base polymer and its gel strength influence the absorbency rate of the polymer compositions of the invention. The polymerization method and drying method appear to have the greatest influence on surface characteristics. Absorbent compositions from base polymer particles prepared by the inverse suspension polymerization method generally exhibit a slower absorbency rate than solution polymerized oven and drum dried polymers.

Low gel strength base polymers exhibit a tendency to gel block and for this reason a gel strength (shear modulus) of at least 30,000 dynes/cm$^2$, preferably 40,000 dynes/cm$^2$ or higher is preferred in the base polymer. Reduction in absorbency caused by unfavorable surface characteristic and/or low gel strength can be compensated for by adjusting the particle size prior to agglomeration and by the use of inert, inorganic additives which is explained below.

The gel strength of the absorbent base polymers used in this invention is determined by measuring the shear modulus of the polymer in its hydrated state. The shear modulus of hydrate polymer is determined using stress rheometer and the following procedure can be used to determine the gel strength or shear modulus of the base polymer.

The amount of base polymer required to fully absorb and retain 20 grams of 0.9 weight percent saline solution is determined based on the centrifuge retention capacity of the polymer. Centrifuge retention is measured by placing 0.2 grams of polymer in a test tea bag formed from 6×12 cm strips of tea bag stock which are sealed so that the inside edges of the seals are about 3–5 mm from the edge of the tea bag. Five such tea bags are prepared containing the polymer and two empty blank tea bags. The tea bags are then sealed and placed in a plastic container containing 0.9% saline solution which is 1.5 inches in depth. After soaking for 20 minutes, the tea bags are removed from the saline solution and allowed to drip dry for 5 minutes. Two bags containing the sample and two blanks are then placed in a centrifuge and centrifuged at 1500 RPM for 3 minutes using a Fisher Deluxe Dynac II Centrifuge. The tea bags (samples and blanks) are then weighed. The weight of the blank is subtracted from the weight of the sample and the weight of dry sample subtracted from this remainder. The resulting remainder is then divided by the weight of dry sample and this value is reported as centrifuge retention in g/g.

A stress rheometer manufactured by Rheometrics Incorporated of Piscataway, N.J. called a Rheometrics Fluid Spectrometer Model 8400 (RFS-8400) is used to measure the shear modulus value of base polymer.

The Rheometrics Fluid Spectrometer Model 8400 (RFS-8400) characterizes rheological properties of a gel using dynamic oscillatory and steady shear tests under conditions of controlled strain, and frequency of shear rate.

The user selects the test geometry appropriate to the material to be tested, and the deformation history to be applied to the sample. Test modes include: single, rate sweep, thixotropic loop and step rate in steady shear; single, frequency sweep, time sweep, steady/dynamic and step strain in dynamic. The microprocessor translates the strain and frequency history into motion of the serve-controlled motor based upon the geometry used. The sample temperature history is controlled during the test using recirculating fluid in the environmental chamber.

The torque generated in response to the imposed motion is measured by the tranducer. The microprocessor calculates stress from this value and combines this value with measured sample motion to calculate strain and gererate values of the selected rheological properties.

The amount of base polymer to be tested is determined from the amount of polymer which freely absorbs and retains 20 grams of a 0.9% NaCl (saline) solution to create swollen hydrogels which is calculated from its centrifuge retention value. Excess fluid from the hydrogels is removed by blotting on absorbent paper material. Fifteen grams of the hydrogel material is then placed in the rheometrics cup which fits the 25 mm bottom plate of the measuring device. The material is spread evenly over the bottom surface of the cup. The cup is then seated onto the bottom plate. The top plate is then lowered until a gap of 2.50 mm is reached. The test is then conducted under these conditions.

| PARAMETER | VALUE |
| --- | --- |
| Type of Rheometer | Rheometrics RFS 8400 |
| Mode | single |
| Geometry | Parallel Plates |
| Rate | 470 + 0 Hertz |
| Strain | 01 + 0 |
| Steady | Dynamic |
| Strain Offset | 0 |
| Plate Radius | 25 mm |

| PARAMETER | VALUE |
| --- | --- |
| Temperature | 20° C. |

The shear modulus determined at these conditions is a calculation of the ratio of the applied stress to the amplitude of the in phase component of the resultant strain.

Surface crosslinking and agglomeration renders all particles into a high absorbency rate composition. However, in practical application, it is preferred that the particle size distribution of the agglomerated absorbent compositions of the invention be such that more than 50 percent of the particles are at least 150 microns and less than 20 percent smaller than 75 microns. This particle size distribution is preferred for two reasons: (1) elimination of dusting in subsequent manufacturing process for incorporating the absorbent composition into absorbent articles and (2) the elimination of gel blocking in the absorbent composition itself.

Gel blocking is an apparent reduction in fluid absorption properties caused by the formation of a highly fluid gel which encompasses or surrounds unwetted particles and prevents fluid transport to the absorbent particles surface. Gel blocking can be eliminated in the absorbent composition of the invention by uniform surface crosslinking of the base polymer, by the elimination of fine particles less than 75 microns in size and by the use of inert, inorganic, non-hydrophobic, water insoluble compounds having a particle size of 150 microns or less and an apparent density less than 0.5 ml per gram. The apparent density of such inert inorganic compounds is determined in accordance with ASTM B-212-82.

The absorbent base polymers useful in the invention are known. They may be selected from a crosslinked, partially neutralized polyacrylic acid (see U.S. Pat. No. 4,654,039), a crosslinked, partially neutralized starch-acrylic acid graft polymer (U.S. Pat. No. 4,076,663), a crosslinked, partially neutralized copolymer of isobutylene and maleic anhydride (U.S. Pat. No. 4,389,513), a sponification product of vinyl acetate-acrylic acid copolymer (U.S. Pat. No. 4,124,748), a hydrolyzate of acrylamide polymer or acrylamide copolymer (U.S. Pat. No. 3,959,569) or a hydrolyzate of an acrylonitrile copolymer (U.S. Pat. No. 3,935,099). The teachings of the above patents are hereby incorporated by reference. All of the above described fluid absorbent base polymers can be used to make absorbent compositions within this invention as well as any fluid absorbent polymer provided the base polymer has a free absorbency of at least 3 ml/gm.

The partially neutralized, crosslinked, fluid absorbent described above, should have at least 50 mole percent of the free acid groups neutralized for use in preparing absorbent articles such as diapers, incontinent devices, sanitary napkins, etc. Although studies have shown the absorbency rate increases with increased neutralization, absorbent base polymers with 50–95 mole percent neutralization may be used to produce high absorbency rate compositions within the invention. Neutralization of free acid groups within the base polymer can be conducted prior to polymerization or subsequent thereto by known methods using an alkali metal hydroxide or ammonia.

Similarly internal crosslinking of the base polymer during and/or subsequent to the polymerization reaction is known. Internal crosslinking renders the absorbent base polymer substantially insoluble in water. Internal crosslinking agents are generally used in an amount of about 0.001 to 5 weight percent and they are selected from polyvinyl monomers having at least two reactive vinyl groups, vinyl monomers having one reactive vinyl group and at least one functional group which is reactive with at least one of the monomers in the polymerization mixture and compounds containing at least two functional groups which are reactive with at least one of the polymerization monomers.

The base polymer described above may be prepared by a variety of known polymerization methods, i.e. solution, suspension and emulsion processes; preferably aqueous solution polymerization or inverse suspension polymerization in an organic solvent. The aqueous solution method is described in a variety of patents; see for example U.S. Pat. Nos. 4,654,039; 4,076,663; 4,286,082 and 4,525,527. Similarly, the inverse suspension method is described in U.S. Pat. Nos. 4,340,706 and 4,506,052. The teaching of the above cited patents are hereby incorporated by reference.

In accordance with the process of the invention, an absorbent base polymer having a free absorbency of 30 ml/gm, of a predetermined particle size is contacted with an aqueous solution of a crosslinker under high intensity mixing conditions to surface crosslink the absorbent base polymer particles and to agglomerate them into larger-sized particles. As used in this description surface crosslinking means that the polymer chains in the vicinity or near the surface of the polymer are crosslinked. After agglomeration, the composition may be optionally screened to remove over and under sized particles; both of which may recycle after the oversized particles are ground.

The aqueous crosslinker solution may be used in an amount of from about 1 to 20 percent based upon the weight of absorbent base polymer; preferably about 3 to 10 percent. The crosslinker content of the solution is from about 0.05 to 10 percent based upon the weight of absorbent base polymer.

Effective surface crosslinkers are polyvalent metal salts, oxides, hydroxides and other compounds which are soluble in water and which dissociate in water. In addition, organic amines and polyimines have been found to be effective ionic crosslinkers. Although heating is generally not necessary, the base polymer may be optionally heated during the crosslinking and agglomeration process.

The crosslinking and agglomeration of the absorbent base polymer can be generally conducted at room temperature with the crosslinker solution applied in a manner such that the solution is uniformly distributed on the surface of the base polymer. Any of the known means for dispersing a liquid can be used preferably uniformly dispersing a liquid into fine liquid droplets; e.g., a pressurized nozzle, a two fluid spray nozzle or a rotating disc. The crosslinker solution is contacted with the base polymer under mixing condition; preferably high intensity mixing conditions.

In order to effect agglomeration of the base polymer, it has been found that high intensity mixing is required. Uniform crosslinker dispersion and particle agglomeration can be achieved with a high intensity mechanical mixer or a fluid mixer which suspends the powder in a turbulent gas stream. Low power drum tumblers and other similar low energy mixers do not impart enough energy into the moistened particles to effect agglomeration. Methods for the dispersion of a liquid onto an absorbent base polymer's surface and particle agglomeration are known in the art; see for example U.S. Pat. No. 4,734,478 the teachings of which are hereby incorporated by reference; in particular column 6, line 45 to column 7, line 35.

Exemplary commercially available equipment for conducting the agglomeration step of the invention are single high speed variable intensity paddle mixers such as the Turbulizer mixer of the Bepex Corporation, Rolling Meadows, Ill.; or the high speed variable intensity vertical mixer sold by Bepex under the tradename Turboflex. These machines are generally operated in a continuous manner using a short residence time in the order of 2 seconds to 2 minutes, typically 2–30 seconds. Agglomeration may be effected batchwise in a high intensity mixer such as a Henschel mixer. In any event whether a batchwise or continuous agglomeration method is used, simple experimentation can be conducted to determine the best process conditions for the particular machine employed in the process. Preferably, the surface crosslinking and particle agglomeration are conducted under high intensity mixing conditions. However, the surface crosslinker solution may uniformly dispersed on the base particles' surfaces and then the moistened particles are subjected to high intensity mixing to effect their agglomeration.

The surface crosslinking of the absorbent base polymers used in the invention is known; see for example U.S. Pat. Nos. 4,043,952 and 4,259,987; the teachings of which are hereby incorporated by reference. The surface crosslinking of the base polymer is accomplished by ionic bonding of reactive groups in the base polymer with a polyvalent metal cation, an amine or a polyimine. The polyvalent metal may be selected from the metals of Groups IIA–VIA, IB–IIB and VII of the Periodic Table. Salts, oxides, hydroxides and other compounds of such metals may be used provided: (1) the compound is soluble in water (2) the compound ionizes or dissociates in water and (3) the metal cation, amine or imine has a reactive valence of at least two. Exemplary polyvalent cations are those of the metals: aluminum, copper, zinc, zirconium, iron, cobalt, chromium and titanium. A preferred cation is that of aluminum. Exemplary compounds containing these cations are: aluminum sodium sulfate, aluminum sulfate, poly-aluminum chloride, aluminum diacetate, basic aluminum hydroxide (1:1 mole ratio of aluminum hydroxide and sodium hydroxide), cobalt acetate, cupric sulfate, zinc acetate, zirconium acetate, zirconium tetrachloride and zirconium nitrate. Useful amine and imine compounds are those which are water soluble and ionize in water. Preferred amines are those containing at least two amino or imino groups such as ethylene diamine and polyethyleneimine.

Aluminum sodium sulfate is a preferred ionic crosslinker. However, the number of compounds useful for this step of the process is large, and a satisfactory ionic crosslinker can be easily found by simple experimentation. Two compounds which were found to be ineffective in our studies were magnesium sulfate and boron hydroxide.

The absorbency rate of the compositions of the invention may be improved by the addition of an inert, inorganic, non-hydrophobic, water insoluble compound having a particle size of 150 microns or less (preferably less than 150 microns) and an apparent density of less than 0.5 gm/ml. These additives are added to the compositions of the invention after they have been crosslinked and agglomerated. The additive is uniformly dispersed on the surface of the agglomerated particles by standard blending techniques. Optionally the blending step may be conducted after classification of the crosslinked and agglomerated particles of the invention into a preferred particle size distribution. Inorganic additives should not be added during the crosslinking and agglomeration step.

Exemplary inert inorganic useful in the practice of the invention are titanium oxide-C (average particle size—20 nanometer, BET surface area—100 $m^2/g$, apparent density 0.10 g/ml); titanium oxide—Fischer (average particle size 300 nanometer, apparent density 0.43 g/ml); swellable attapulgite clay (average particle size—140 nanometer, BET—200 $m^2/g$, apparent density—0.32 g/ml); aluminum oxide—Kyoward (average particle size—20,000 nanometer, BET—150 $m^2/g$, apparent density—0.27 ml/g); fumed silica—Cabosil M-5 (average particle size—14 nanometer, BET—200 $m^2/g$, apparent density—0.04 g/ml); fumed silica—Cabosil EH-5 (average particle size—8 nanometer, BET—380 $m^2/g$, apparent density—0.04 g/ml).

Generally, the inorganic additive described above may be used in an amount of about 0.5 to about 20 percent by weight; preferably 0.5 and 10 percent, more preferably 1.0 to 5 percent and most preferably about 1 to 3 percent. The addition o additives above 30 percent tends to reduce the apparent absorbency rate of the composition because of reduction in the amount of absorbent polymer in the composition.

Additives which find use in improving the absorbency rate of the composition of the invention are fumed silicia, aluminum hydroxide, titanium oxide, swellable clay, etc. It was found that the particle size, apparent density and hydrophillic characteristics of such inorganic compounds are controlling factors in obtaining improved absorbency rate and not the chemical composition of the additive.

The following examples illustrate the invention:

EXAMPLE 1

A water-absorbent, commercially available, crosslinked, partially neutralized starch-acrylic acid graft polymer (IM-1000 from Hoechst Celanese Corporation) was screened into particle size ranges as set forth in the following table. A typical analysis of this product prior to crosslinking and agglomeration is as follows: total absorbency (g/g in 0.9% saline)—65 and gel strength (shear modulus)—35,000 dynes/$cm^2$. A portion of each fraction was surface crosslinked and agglomerated and the absorbency rate determined on each fraction (treated and untreated) which is reported below.

The following procedure was used to effect the surface crosslinking and agglomeration of each fraction. In a high speed laboratory blender (12,000 RPM) having a volume of 1200 ml were placed 30 grams of each absorbent polymer fraction. A 10 weight percent solution of aluminum sodium sulfate [AlNa $(SO_4)_2$ $12H_2O$] in water was prepared and using a syringe, 1.5 grams of this solution (5% of crosslinker solution containing 0.5% crosslinker both based on weight of polymer) was injected into the agitating polymer. After completion of the aluminum sodium sulfate addition, the mixer was turned off and the polymer was allowed to stand at room temperature for approximately 40 minutes. It was then screened, if necessary, into a particle size corresponding to its original particle size. Aerosil 200, a fine silicon dioxide powder was then blended into the treated polymer fraction by mixing the materials in a small plastic bag.

| IM - 1000 Absorbency Rate | | | |
|---|---|---|---|
| Particle Size Mesh | Untreated Sec. | Treated Sec. | Treated Sec. |
| 50–100 | 35 | 32.3 | 32.1 |
| 100–140 | 27 | 18.1 | 15.2 |
| 140–200 | 60.1 | 10.1 | 8.2 |
| 200–325 | — | 8.4 | 6.2 |
| < 325 | — | 6.8 | 5.6 |
| Aerosil 200*-% | 0 | 1 | 2 |

*Aerosil 200 is a finely divided silicon dioxide produced by the Japan Aerosil Co., Ltd.

EXAMPLE 2

The procedure of Example 1 was repeated except a water-absorbent commercially available, crosslinked, partially neutralized starch-acrylic acid graft polymer designated IM-1500 available from Hoechst Celanese Corporation was used. A typical analysis of this polymer prior to treatment is as follows: total absorbency (g/g in 0.9% saline)—45 and gel strength (shear modulus)—65,000 dynes/cm$^2$.

| IM - 1500 Absorbency Rate | | |
|---|---|---|
| Particle Size Mesh | Untreated Sec. | Treated Sec. |
| 50–100 | 37.2 | 33.8 |
| 100–140 | 25.0 | 15.2 |
| 140–200 | 38.0 | 8.7 |
| 200–325 | 69.6 | 6.0 |
| <325 | — | 4.8 |
| Aerosil 200-% | 0 | 1 |

EXAMPLE 3

The procedure of Example 1 was repeated using a commercially available starch-acrylic acid graft polymer designated IM-5000P available from Hoechst Celanese Corporation. Typical properties of this absorbent polymer are as follows: total absorbency (g/g in 0.9% saline)—45 and gel strength (shear modulus)—80,000 dynes/cm$^2$.

| IM - 5000 P Absorbency Rate | | |
|---|---|---|
| Particle Size Mesh | Untreated Sec. | Treated Sec. |
| 50–100 | 37 | 34.3 |
| 100–140 | 25.9 | 15.6 |
| 140–200 | 42.1 | 8.8 |
| 200–325 | 75.8 | 6.2 |
| <325 | — | 4.8 |
| Aerosil 200-% | 0 | 1 |

EXAMPLE 4

The procedure of Example 1 was repeated using a commercially available, crosslinked, partially neutralized, polyacrylic acid polymer designated IM-5000S available from Sanyon Chemical Industries, Ltd., Kyoto, Japan. Typical properties of this polymer are as follows: total absorbency (g/g in 0.9 saline)—47 and gel strength (shear modulus)—65,000 dynes/cm$^2$.

| IM - 5000 Absorbency Rate | | |
|---|---|---|
| Particle Size Mesh | Untreated Sec. | Treated Sec. |
| 50–100 | 37.2 | 35.1 |
| 100–140 | 26.8 | 15.8 |
| 140–200 | 42.6 | 8.2 |
| 200–325 | 71.0 | 6.3 |
| <325 | — | 5.1 |
| Aerosil 200-% | 0 | 1 |

EXAMPLE 5

The procedure of Example 1 was repeated except a commercially available, water absorbent, crosslinked, partially neutralized, isobutylene-maleic anhydride copolymer designated KI Gel, by Kuraray Ltd., Japan. Typical properties of this polymer are as follows: total absorbency (g/g in 0.9 saline)—41 and gel strength (shear modulus)—50,000 dynes/cm$^2$.

| KI Gel Absorbency Rate | | |
|---|---|---|
| Particle Size Mesh | Untreated Sec. | Treated Sec. |
| 50–100 | — | 35.2 |
| 100–140 | — | 20.1 |
| 140–200 | — | 12.5 |
| 200–325 | — | 7.0 |
| <325 | — | 5.8 |
| Aerosil 200-% | 0 | 1 |

EXAMPLE 6

The procedure of Example 1 was repeated using a commercially available polyvinyl alcohol-sodium acrylate copolymer, designated Sumika Gel, from Sumitomo Chemical Co. Ltd., Japan. Typical properties of this polymer are as follows: total absorbency (g/g in 0.9 saline)—52 and gel strength (shear modulus)—30,000 dynes/cm$^2$.

| Sumika Gel Absorbency Rate | | |
|---|---|---|
| Particle Size Mesh | Untreated Sec. | Treated Sec. |
| 50–100 | — | 55.8 |
| 100–140 | — | 30.4 |
| 140–200 | — | 19.8 |
| 200–325 | — | 13.0 |
| <325 | — | 9.7 |
| Aerosil 200-% | 0 | 1 |

EXAMPLE 7

The following experiment was conducted to show the effect of particle size on absorbency rate. A sample of the absorbent polymer designated IM 5000S from Sanyo (a starch-acrylic acid graft polymer), having a particle size distribution such that 100 percent of the polymer passed through a 50 mesh screen, was tested. This polymer was screened into individual fractions containing successively higher proportions of polymer less than 100 mesh (150 microns) and each fraction was surface crosslinked and agglomerated and blended with finely divided silicon dioxide (1%) in accordance with the procedure of Example 1. The absorbency rate was determined for each fraction and reported below.

| Particle Size <100 Mesh Weight Percent | Absorbency Rate Sec. |
|---|---|
| 30 | 24 |
| 40 | 18.9 |
| 50 | 15.5 |
| 60 | 11.9 |
| 70 | 9.9 |

An absorbency rate of 20 seconds or less was achieved when 40 percent of particles had a particle size of 150 microns or less.

EXAMPLE 8

Polymers produced by different polymerization procedures and drying methods were evaluated to determine the effect of shape and surface characteristics on absorbency rate. Polymer A was a polyacrylate absorbent polymer of spherical particle shape made by the inverse suspension polymerization method from Seitetsu, Osaka, Japan. Polymer B was a polyacrylate absorbent polymer that was solution polymerized and oven dried. Polymer C was a starch grafted polyacrylate polymer that was solution polymerized and drum dried.

Polymers A, B, and C were screened and divided into the following fractions:

| Fraction | Particle Size Distribution Mesh | | | | | |
|---|---|---|---|---|---|---|
| | 50–80 | 80–100 | 100–140 | 140–200 | 200–350 | 350 P |
| 50 P | 17% | 17% | 17% | 17% | 16% | 16% |
| 80 P | — | 20% | 20% | 20% | 20% | 20% |
| 100 P | — | — | 25% | 25% | 25% | 25% |
| 140 P | — | — | — | 34% | 33% | 33% |
| 200 P | — | — | — | — | 50% | 50% |
| 325 P | — | — | — | — | — | 100% |

Each of the above fractions were crosslinked, agglomerated and blended with 1% silicon dioxide according to the procedure of Example 1. The absorbency rate on each fraction was determined and is reported below.

| Particle Size Mesh | Absorbency Rate | | |
|---|---|---|---|
| | Polymer A Sec. | Polymer B Sec. | Polymer C Sec. |
| 50 P | 35.9 | 27.2 | 20.4 |
| 80 P | 27.7 | 20.6 | 14.0 |
| 100 P | 21.6 | 15.6 | 9.6 |
| 140 P | 15.8 | 10.8 | 6.9 |
| 200 P | 11.4 | 8.7 | 5.8 |
| 325 P | 9.0 | 7.8 | 5.1 |

The above data illustrates particle shape has an influence on the absorbency rate with the spherically shaped polymer particles giving the slowest rate; the oven dried particles an intermediate value and the drum dried particles producing the fastest absorbency rate.

EXAMPLE 9

A surface crosslinked and agglomerated absorbent polymer was prepared generally in accordance with the procedure of Example 1 using various crosslinking agents from crosslinked, partially neutralized polyacrylic acid base polymer particles having a particle size such that all particles passed through a 145 mesh screen. The identity of the crosslinking agents and the absorbency rate of the resulting polymer composition is reported below. The value of temperature and time reported below are the temperature under which the crosslinking and agglomeration steps were conducted and the time before the absorbency rate testing was done; respectively

| Crosslinker | Absorbency Rate - Sec.* | |
|---|---|---|
| | 20–30° C. - 1 hr. | 100° C. 1 hr. |
| none - control | 67.2 | 65.1 |
| AlNa(SO$_4$)$_2$ 12H$_2$O | 6.2 | 6.4 |
| Al$_2$(SO$_4$)$_3$ 13.7H$_2$O | 6.4 | 6.3 |
| Poly-AlCl$_3$ | 6.7 | 6.5 |
| Al(OH)$_3$ + NaOH (1 mole:1 mole) | 6.5 | 6.6 |
| Aluminum acetylacetonate | 67.2 | 63.2 |
| (CH$_3$CO$_2$)$_2$AlOH | 9.6 | 7.1 |
| MgSO$_4$ | 64.3 | 7.6 |
| MgSO$_4$ + NaOH(1 mole:1 mole) | 65.1 | — |
| MgSO$_4$ + H$_2$SO$_4$(1 mole:1 mole) | 67.4 | — |
| B(OH)$_3$ | 62.3 | 60.6 |
| B(OH)$_3$ + NaOH(1 mole:1 mole) | 67.2 | 65.6 |
| B(OH)$_3$ + H$_2$SO$_4$(1 mole:1 mole) | 66.4 | 65.1 |
| CaCl$_2$ | 63.1 | 7.1 |
| FeSO$_4$ | 6.3 | 6.1 |
| CuSO$_4$ | 8.6 | 6.8 |
| ZrCl$_4$ | 6.1 | 6.3 |
| (NH$_4$)$_3$[Zr(CO$_3$)$_3$OH] | 65.6 | 62.1 |
| CoCl$_2$ | 9.2 | 6.8 |
| Ethylene glycol diglycidyl ether | 60.3 | 7.1 |
| Ethylene glycol | 61.2 | 57.6 (7.8)** |
| Ethylene diamine | 7.2 | 6.8 |
| Polyethylene imine | 6.5 | 6.6 |

*all samples except control contained 1% silicon dioxide
**3 hours at 180° C.

The above data shows that the ionic crosslinkers (excluding CaCl, MgSO$_4$, B(OH)$_3$) work quite well at room temperature while polyhydroxy compounds such as ethylene glycol require heat to effect the surface crosslinking.

EXAMPLE 10

The final particle size of the crosslinked and agglomerated absorbent has an effect on the absorbency rate of the products of the invention but it does not appear to be the controlling factor. Base polymers corresponding to Polymers A, B and C of Example 8 were screened through a 145 mesh screen and treated according to the procedure of Example 1. The crosslinked and agglomerated products were then separated into the particle size fractions reported below and the absorbency rate for each fraction determined.

| Fraction Mesh | Absorbency Rate - Sec.* | | |
|---|---|---|---|
| | Polymer A | Polymer B | Polymer C |
| 20 P | 15.9 | 11.0 | 7.0 |
| 50 P | 15.8 | 10.9 | 6.9 |
| 100 P | 15.5 | 10.7 | 6.8 |
| 140 P | 15.0 | 10.5 | 6.5 |
| 200 P | 12.3 | 9.5 | 5.9 |
| 325 P | 9.8 | 8.2 | 5.1 |

*1% silicon dioxide - Aerosil 200

EXAMPLE 11

The following table illustrates the effect of varying amounts of crosslinkers on the absorbency rate. The base polymer prior to crosslinking and agglomeration was a crosslinked, partially neutralized polyacrylic acid polymer having a particle size such that all particles passed through a 145 mesh screen. The procedure of Example 1 was used to effect crosslinking and agglomeration.

| Absorbency Rate* | |
|---|---|
| % Crosslinker based on Polymer | Absorbency Rate Sec. |
| Crosslinker - AlNa(SO$_4$)$_2$ 12H$_2$O | |
| 0.05 | 12.3 |
| 0.1 | 8.3 |
| 0.5 | 6.0 |
| 1.0 | 6.2 |
| 2.0 | 6.8 |
| 10.0 | 8.5 |
| Crosslinker - Poly-AlCl$_3$ | |
| 0.05 | 13.3 |
| 0.1 | 8.6 |
| 0.5 | 6.4 |
| 1.0 | 6.7 |
| 2.0 | 7.0 |
| 10.0 | 8.3 |
| Crosslinker - Al(OH)$_3$ + NaOH | |
| 0.05 | 11.1 |
| 0.1 | 8.0 |
| 0.5 | 6.2 |
| 1.0 | 6.5 |
| 2.0 | 7.2 |
| 10.0 | 8.1 |
| Crosslinker - Ethylene Diamine | |
| 0.05 | 10.1 |
| 0.1 | 6.5 |
| 0.5 | 6.8 |
| 1.0 | 7.2 |
| 2.0 | 7.9 |
| 10.0 | 10.2 |
| Crosslinker - Polyethyleneimine | |
| 0.05 | 10.8 |
| 0.1 | 8.3 |
| 0.5 | 6.7 |
| 1.0 | 6.5 |
| 2.0 | 7.2 |
| 10.0 | 8.6 |
| Crosslinker - CuSO$_4$ | |
| 0.05 | 17.2 |
| 0.1 | 13.4 |
| 0.5 | 10.5 |
| 1.0 | 8.6 |
| 2.0 | 9.7 |
| 10.0 | 12.1 |
| Crosslinker - (CH$_3$CO$_2$)$_2$AlOH | |
| 0.05 | 19.8 |
| 0.1 | 14.8 |
| 0.5 | 9.5 |
| 1.0 | 7.6 |
| 2.0 | 7.1 |
| 10.0 | 8.8 |
| Crosslinker - FeSO$_4$ | |
| 0.05 | 15.1 |
| 0.1 | 12.2 |
| 0.5 | 7.4 |
| 1.0 | 6.3 |
| 2.0 | 7.2 |
| 10.0 | 9.8 |

*all samples contained 1% - Aerosil 200

EXAMPLE 12

The following example was conducted to illustrate the effect of the amount of crosslinker solution. The base polymer was the same as used in Example 11. The surface crosslinker was aluminum sodium sulfate and the amount of crosslinker was 0.5 percent based on the weight of absorbent base polymer. The crosslinker solution was added to the polymer in amounts ranging from 1 to 20 percent based on the amount of polymer. The procedure of Example 1 was used to crosslink and agglomerate the polymer products and the absorbency rate was determined as reported below.

| Absorbency Rate | | |
|---|---|---|
| Crosslinker Solution Weight % | Ex. 12-1 Sec. | Ex. 12-2 Sec. |
| 1 | — | 22.3 |
| 3 | — | 15.1 |
| 5 | 65.2 | 7.6 |
| 7 | 32.0 | 6.8 |
| 10 | 16.1 | 6.4 |
| 20 | 12.0 | 6.6 |
| Aerosil 200 | 0 | 1.0 |

EXAMPLE 13

Various inorganic and organic additives were added to surface crosslinked and agglomerated products prepared by the process of this invention. The base polymer was a crosslinked, partially neutralized starch grafter polyacrylic acid polymer which was surface crosslinked and agglomerated using a Hosokawa Turbulizer, a high intensity paddle mixer produced by the Hosokawa Iron Works, Ltd., Osaka, Japan. The following table sets forth the effect of these various additives on the absorbency rate of the polymer. All experiments were conducted using 10 percent by weight of inorganic additive based upon the weight of absorbent polymer.

| Additive Effect | | | |
|---|---|---|---|
| Additive | Designation | Remarks | Absorbency Rate |
| none | | | 62.1 |
| SiO$_2$ | Aerosil - 200 | Hydrophillic silica | 8.3 |
| SiO$_2$ | Zeolex - 7 | Hydrophillic silica | 10.1 |
| SiO$_2$ | Cab-O-Sil M-5 | Hydrophillic silica | 9.6 |
| SiO$_2$ | Cab-O-Sil EH-5 | Hydrophillic silica | 8.0 |
| SiO$_2$ | Aerosil - 972 | Hydrophillic silica | <60 |
| SiO$_2$ | Cab-O-Sil TS - 720EH-5 | Hydrophillic silica | <60 |
| Al(OH)$_3$ | Catapal XD | no data | 38.0 |
| Al(OH)$_3$ | Kyoward 200 | — | 9.8 |
| Al(OH)$_3$ | Aluminum Oxide - C | — | 8.5 |
| TiO$_2$ | TiO$_2$ (Fisher) | — | 13.4 |
| TiO$_2$ | Titanium Oxide - C | — | 8.5 |
| Swellable Clay | Attagel - 40 | Attapulgite Clay | 12.1 |
| Unswellable Clay | — | — | 29.1 |
| PVA | PVA - 117 (Kuraray) | Saponified degree 100% | >60 |
| PVA | PVA - 217 (Kuraray) | Saponified degree 100% | >60 |
| Aluminum Stearate | (Sakai Chemical) | Hydrophobic Compound | >60 |

The above data illustrates the general usefulness of inert, hydrophillic, inorganic additives, (within the parameter previously defined), to obtain high absorbency rate.

The fluid absorbent polymer compositions of the invention may be used in the manufacturing of absorbent articles such as diapers, sanitary napkins, incontinent devices and other fluid absorbent articles. Articles of these forms and their fabrications are fully described in various U.S. Patents including: U.S. Pat. Nos. 3,952,194, issued July 13, 1971; 3,489,148, issued Jan. 13, 1970; 3,860,003, issued Jan. 14, 1975; and 3,871,378, issued Mar. 18, 1975; the teachings of which are hereby incorporated by reference.

The incorporation of the polymer compositions of this invention into these absorbent articles can be effected in any of the conventional manners by combining them with various types of hydrophillic materials in order to form improved absorbent structures. Examples of hydrophillic materials include cellulose, rayon and polyester fibers and surfactant treated or silica treated thermoplastic foams, films and fibers.

The absorbent article can comprise an intimate admixture of hydrophillic material and the fluid absorbent polymer compositions of the invention with the absorbent polymer being distributed essentially uniformly throughout the hydrophillic material. Alternately, the fluid absorbent polymer compositions of the invention can be dispersed into at least one or more layers between the hydrophillic material. Another alternative can be to form a laminate by over-wrapping the fluid absorbent polymer compositions of the invention with sheets of hydrophillic material such as tissue paper, if desired.

What is claimed is:

1. A process for preparing a water absorbent polymer composition having an absorbency rate of 20 seconds or less comprising; (a) introducing a water absorbent base polymer having a free absorbency of at least 30 ml/gm and a particle size distribution such that 100 percent of said particles are 150 microns or less into a mixing zone; (b) uniformly contacting the surface of the absorbent base polymer with an aqueous crosslinker solution in an amount of from about 1 to about 20 percent by weight based upon the weight of said base polymer; said crosslinker solution containing from about 0.05 to about 10 percent by weight of a ionic crosslinker selected from an inorganic or an organic compound capable of providing an ionizable metal cation, an amino cation or an imino cation having a valence of at least two; and (c) subjecting the absorbent base polymer and crosslinking solution to a high intensity mixing to crosslink the surface of said base polymer particles and agglomerated said base polymer particles into particles of larger size.

2. A water absorbent polymer composition made in accordance with the process of claim 1.

3. A water absorbent polymer composition made in accordance with the process of claim 2 containing from about 0.5 to about 20 percent of an inert, inorganic, hydrophillic, water insoluble compound which is added to said composition after said agglomeration and crosslinking step and wherein said inert, inorganic compound has a particle size of 150 microns or less and an apparent density of less than about 0.5 g/ml.

4. A process according to claim 1 wherein said base polymer particles have a particle size of 150 microns or smaller and wherein said base polymer has a gel strength of 30,000 dynes/cm$^2$ or higher.

5. A water absorbent polymer composition made in accordance with the process of claim 4.

6. A water absorbent composition made in accordance with the process of claim 5 containing from about 1 to about 5 percent of an inert, inorganic, hydrophillic, water insoluble compound which is added to said composition after said agglomeration and crosslinking step and wherein said inert, inorganic compound has a particle size of 150 microns or less and an apparent density of less than about 0.5 g/ml.

7. An absorbent article comprising an absorbent composition according to claim 5 and in the amount of 2 to about 50 percent by weight of said article and about 50 to 98 percent by weight of a hydrophillic fiber based upon the weight of said structure.

8. An absorbent article comprising a liquid impermeable backing sheet, a liquid permeable top sheet and a core of an absorbent article according to claim 7 positioned between said backing and top sheet.

9. A process according to claim 1 wherein said base polymer particles have a particles size of 100 microns or smaller and wherein said base polymer has a gel strength of 30,000 dynes/cm$^2$ or higher.

10. A water absorbent polymer composition made in accordance with the process of claim 9.

11. A water absorbent composition made in accordance with the process of claim 10 containing from about 1 to about 5 percent of an inert, inorganic, hydrophillic, water insoluble compound which is added to said composition after said agglomeration and crosslinking step and wherein said inert, inorganic compound has a particle size of 150 microns or less and an apparent density of less than about 0.5 g/ml.

12. A process according to claim 1 wherein at least about 90 percent by weight of said base polymer particles are within the range of 75-150 microns in size and wherein said base polymer has a gel strength of 30,000 dynes/cm$^2$ or higher.

13. A water absorbent polymer composition made in accordance with the process of claim 12.

14. A water absorbent composition made in accordance with the process of claim 13 containing from about 1 to about 5 percent of an inert, inorganic, hydrophillic, water insoluble compound which is added to said composition after said agglomeration and crosslinking step and wherein said inert, inorganic compound has a particle size of 150 microns or less and an apparent density of less than about 0.5 g/ml.

15. A process according to claim 1 wherein said ionic crosslinker is selected from a salt, oxide or hydroxide of aluminum.

16. A water absorbent polymer composition made in accordance with the process of claim 15.

17. A water absorbent composition made in accordance with the process of claim 16 containing from about 1 to about 5 percent of an inert, inorganic, hydrophillic, water insoluble compound which is added to said composition after said agglomeration and crosslinking step and wherein said inert, inorganic compound has a particle size of 150 microns or less and an apparent density of less than about 0.5 g/ml.

18. A process according to claim 1 wherein said ionic crosslinker is aluminum sodium sulfate or a hydrate thereof.

19. A water absorbent polymer composition made in accordance with the process of claim 18.

20. A water absorbent composition made in accordance with the process of claim 19 containing from about 1 to about 5 percent of an inert, inorganic, hydrophillic, water insoluble compound which is added to said composition after said agglomeration and crosslinking step and wherein said inert, inorganic compound has a particle size of 150 microns or less and an apparent density of less than about 0.5 g/ml.

21. A process according to claims 1, 4, 9, 12, 15, 18 or 21 comprising the further step of adding after crosslinking and agglomerating said base polymer particles from about 0.5 to about 20 percent of a inert inorganic, hydrophillic, water insoluble compound to said surface crosslinked and agglomerated base polymer and wherein said insert inorganic compound has an average particle size of 150 microns or less and an apparent density of less than about 0.5 g/ml.

* * * * *

UNITED STATES PATENT AND TRADEMARK OFFICE
CERTIFICATE OF CORRECTION

PATENT NO. : 5,002,986
DATED : March 26, 1991
INVENTOR(S) : Yoji Fujiura et al

It is certified that error appears in the above-identified patent and that said Letters Patent is hereby corrected as shown below:

Column 5, Line 52, -- 3 ml/gm -- should read -- 30 ml/gm --

Column 8, Line 28, -- o -- should read -- of --

Column 9, Line 65, -- Sanyon -- should read -- Sanyo --

Column 14, Line 21, -- grafter -- should read -- grafted --

Signed and Sealed this

Sixth Day of October, 1992

Attest:

DOUGLAS B. COMER

*Attesting Officer*  *Acting Commissioner of Patents and Trademarks*